United States Patent
Elahi

(10) Patent No.: US 10,383,764 B2
(45) Date of Patent: Aug. 20, 2019

(54) EYELID IMPLANT DEVICE

(71) Applicant: Ebrahim Elahi, New York, NY (US)

(72) Inventor: Ebrahim Elahi, New York, NY (US)

(*) Notice: Subject to any disclaimer, the term of this patent is extended or adjusted under 35 U.S.C. 154(b) by 60 days.

(21) Appl. No.: 15/798,376

(22) Filed: Oct. 30, 2017

(65) Prior Publication Data

US 2018/0116873 A1 May 3, 2018

Related U.S. Application Data

(60) Provisional application No. 62/414,950, filed on Oct. 31, 2016.

(51) Int. Cl.
| | | |
|---|---|---|
| *A61F 9/007* | (2006.01) | |
| *A61K 9/00* | (2006.01) | |
| *A61F 9/00* | (2006.01) | |

(52) U.S. Cl.
CPC ........ *A61F 9/00718* (2013.01); *A61F 9/0017* (2013.01); *A61F 2220/0008* (2013.01); *A61F 2230/0019* (2013.01); *A61F 2230/0026* (2013.01); *A61F 2250/0015* (2013.01); *A61F 2250/0026* (2013.01); *A61F 2250/0036* (2013.01); *A61K 9/0051* (2013.01)

(58) Field of Classification Search
CPC .................................................. A61F 9/00718
See application file for complete search history.

(56) References Cited

U.S. PATENT DOCUMENTS

| | | | | |
|---|---|---|---|---|
| 4,197,840 A * | 4/1980 | Beck | ................... | A61F 9/00718 600/12 |
| 4,614,413 A * | 9/1986 | Obssuth | ................... | G02C 7/04 351/159.02 |
| 5,322,691 A * | 6/1994 | Darougar | ............. | A61K 9/0051 424/427 |
| 5,542,437 A * | 8/1996 | Blackmore | ......... | A61F 9/00718 128/899 |
| 5,725,493 A * | 3/1998 | Avery | ................... | A61F 9/0017 604/294 |
| 5,823,938 A * | 10/1998 | Hernandez | ............. | A61F 9/007 600/15 |
| 6,482,428 B1 * | 11/2002 | Li | ......................... | A61F 2/0059 424/427 |
| 7,108,718 B1 | 9/2006 | Li et al. | | |
| 2012/0046745 A1 * | 2/2012 | Young | ................. | A61F 9/00718 623/11.11 |
| 2014/0074128 A1 * | 3/2014 | Park | .................... | A61F 9/00727 606/151 |
| 2017/0281408 A1 * | 10/2017 | Arai | ....................... | A61F 9/007 |

* cited by examiner

*Primary Examiner* — David H Willse
*Assistant Examiner* — Javier G Blanco

(57) ABSTRACT

An eyelid implant device adapted for placement under an eyelid includes a body having an upper portion and a lower portion, where the upper portion and the lower portion include an asymmetrical weight distribution, such that the lower portion includes an increased weight distribution relative to the upper portion for facilitating the weighting of the eyelid. A plurality of undulations are located on the outer surface of the trapezoidal shaped body and extend in a direction between opposing parallel bases of the body. The eyelid implant is adapted for placement under the eyelid for weighting the eyelid and facilitating eyelid movement, while the plurality of undulations are adapted to restrict post-operative movement of the eyelid implant device relative to the eyelid by contacting with tissue associated with the eyelid during post-operative healing.

7 Claims, 4 Drawing Sheets

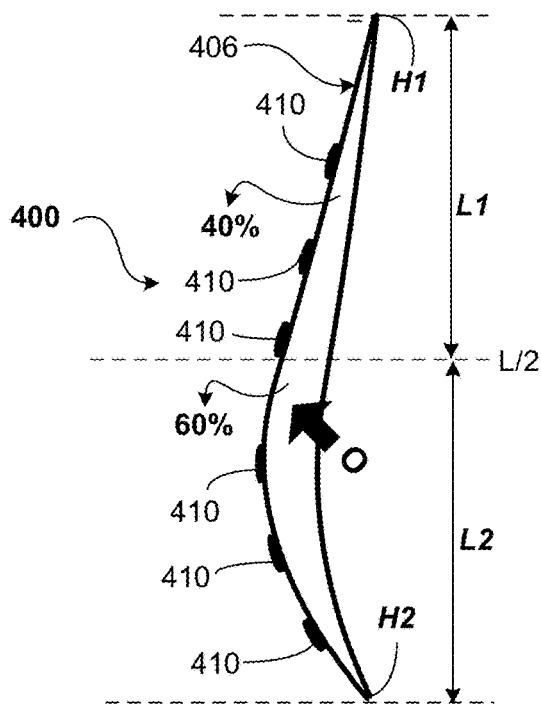
FIG. 4B (A-B)
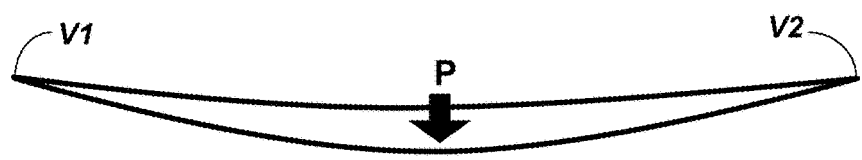
FIG. 4C (C-D)

EYELID IMPLANT DEVICE

CROSS REFERENCE TO RELATED APPLICATION(S)

This application claim priority under 35 USC § 119(e) from provisional application No. 62/414,950, filed on Oct. 31, 2016, the contents of which is hereby incorporated by reference herein its entirety.

BACKGROUND

The present invention generally relates to medical devices, and particularly to surgical implants used in the ocular region.

A large portion of gold or platinum conventional weight implants can post operatively (i.e., following surgical implantation) move over time. In one study this undesirable movement phenomenon was close to 40%. An example of a conventional weight implant 100 for use in a patient's eyelid is shown in FIG. 1. As illustrated in FIG. 2, post-operative movement of the implant 100 may cause a shift in the position of the implant to the outer edge 202 of the patient's eyelid 204. Thus, the current design does not favor stability. Further, the uniformity in shape and thickness of conventionally designed implants, such as that shown in FIG. 1, may create negative cosmetic effects. Such cosmetic effects 300 can be seen in FIG. 3. As depicted, often, patients may have different levels of visible indentations 302, 304, 306, 308 (i.e., mild to prominent) as a result of the implant. Moreover, conventional implants may be susceptible to extrusion, infection, and an inability to maintain weight within the lid.

Referring back to FIG. 1, the method of securing the implant 100 may be via small round holes 102. These small holes 102 make the suturing process more challenging, additionally, leaving little room for the development of scar tissue, which itself contributes to post operatively securing the implant in place.

BRIEF SUMMARY

The following seeks to summarize one or more embodiments of the invention to establish, among other things, an overall understanding of the invention. As such, the summary is not intended to identify key or critical elements, or define any scope associated with either the various embodiments or the claims. Its purpose is to present concepts in a simplified form. According to the one or more exemplary embodiments, a disclosed eyelid weight implant device utilizes, among other things, an asymmetric geometry and various stabilizing features to improve eyelid closure and enhance anti-migration (i.e., post-operative movement) performance.

According to one embodiment, an eyelid implant device adapted for placement under an eyelid may include a trapezoidal shaped body having opposing parallel bases and opposing non-parallel lateral sides. A plurality of undulations (or uneven surface areas) located on the outer surface of the trapezoidal shaped body are provided, whereby the plurality of undulations extend in a direction between the opposing parallel bases. The eyelid implant further includes a corrugated region located along at least a portion of a circumference of the trapezoidal shaped body formed by the opposing parallel bases and opposing non-parallel lateral sides. The eyelid implant is adapted for placement under the eyelid for weighting the eyelid and facilitating eyelid movement, whereby the corrugated region and the plurality of undulations are adapted to restrict post-operative movement of the eyelid implant device relative to the eyelid by contacting with tissue associated with the eyelid during post-operative healing.

According to another embodiment, an eyelid implant device adapted for placement under an eyelid may include a trapezoidal shaped body including an upper portion and a lower portion, such that the upper portion and the lower portion have an asymmetrical weight distribution, whereby the lower portion includes an increased weight distribution relative to the upper portion for facilitating the weighting of the eyelid. The implant further includes a plurality of undulations located on the outer surface of the trapezoidal shaped body, whereby the plurality of undulations are adapted to restrict post-operative yaw movement of the eyelid implant device relative to the eyelid by contacting with tissue associated with the eyelid during post-operative healing.

According to yet another embodiment, an eyelid implant device adapted for placement under an eyelid may include a body including an upper portion and a lower portion, whereby the upper portion and the lower portion have an asymmetrical weight distribution, such that the lower portion includes an increased weight distribution relative to the upper portion for facilitating the weighting of the eyelid. The implant further includes a plurality of undulations located on the outer surface of the body, whereby the plurality of undulations extend in a direction between opposing parallel bases of the body. The eyelid implant is adapted for placement under the eyelid for weighting the eyelid and facilitating eyelid movement, while the plurality of undulations are adapted to restrict post-operative movement of the eyelid implant device relative to the eyelid by contacting with tissue associated with the eyelid during post-operative healing.

BRIEF DESCRIPTION OF THE SEVERAL VIEWS OF THE DRAWINGS

FIG. 4B shows a vertical cross sectional view (along A-B) of the improved exemplary eyelid weight implant device of FIG. 4A; and FIG. 4C shows a horizontal cross sectional view (along C-D) of the improved exemplary eyelid weight implant device of FIG. 4A.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

According to the following described one or more embodiments, an improved exemplary eyelid weight implant device may include several features for, among other things, removing or mitigating some of the undesirable effects described above.

Some of these enhanced features include, without limitation, an increased contact via surface undulation or corrugation and scalloped edges; the introduction of rough surfaces as opposed to a smooth surface design; a substantially trapezoidal or triangular geometry (base down) to minimize thickness; a ballasted profile to allow for asymmetric distribution of weights leading to a minimized rotation or tilt (yaw); enlarged holes to allow for easier placement of sutures, allowing for through-and-through ingrowth of tissue to add stabilization; and tapered edges to allow for reduce edge effects (postoperative cosmetic enhancement). These features will be described below with the aid of FIGS. 4A-4C.

Figure 1:
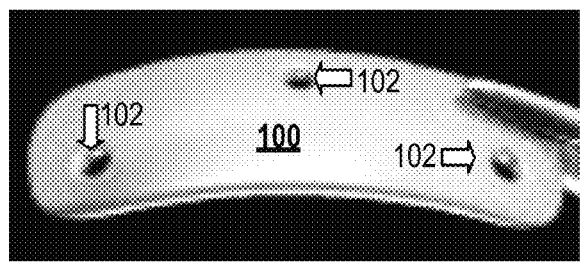
FIG. 1 illustrates an eyelid weight implant device according to a conventional embodiment.
Figure 2:
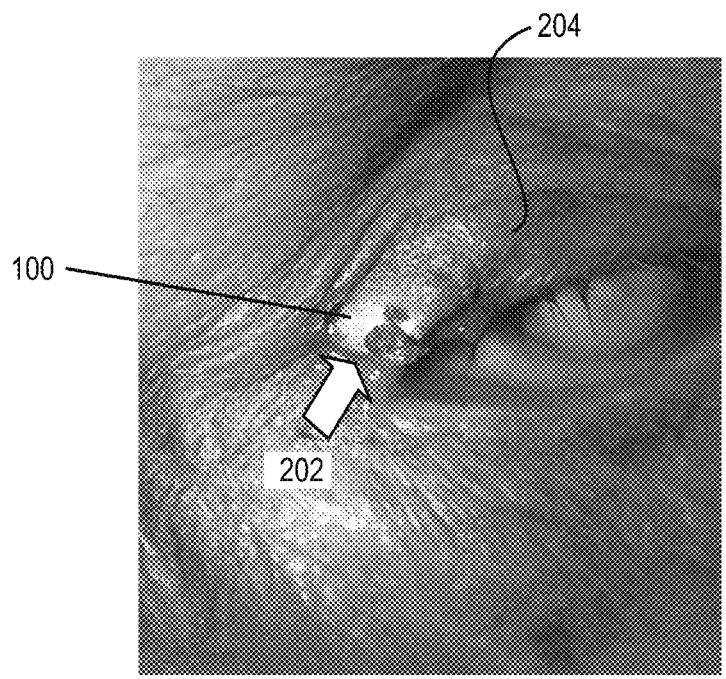
FIG. 2 illustrates the effect of undesirable postoperative migration of some conventional eyelid weight implant devices.
Figure 3:
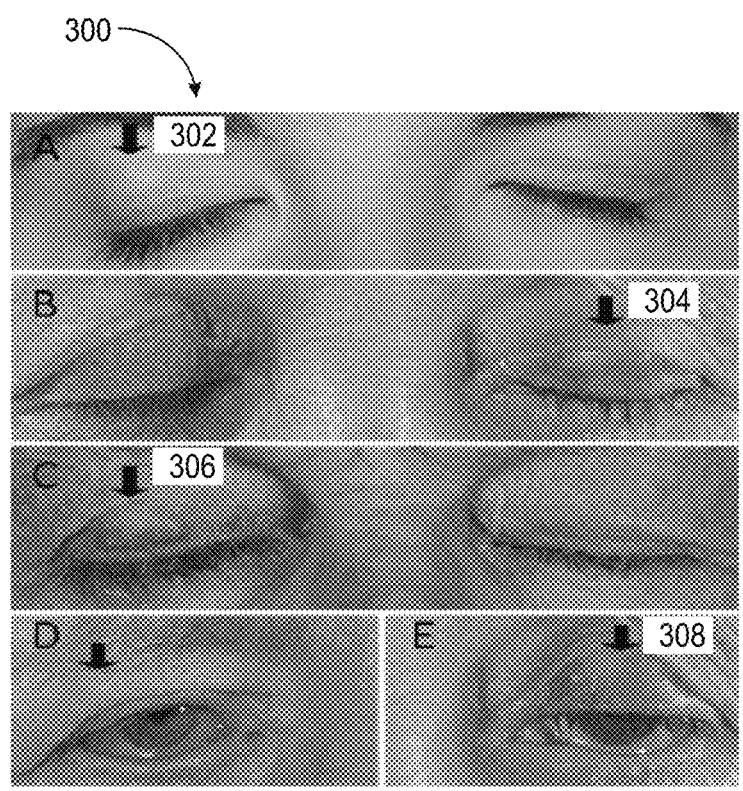
FIG. 3 depicts the cosmetic effects of some conventional eyelid weight implant devices.
Figure 4A:
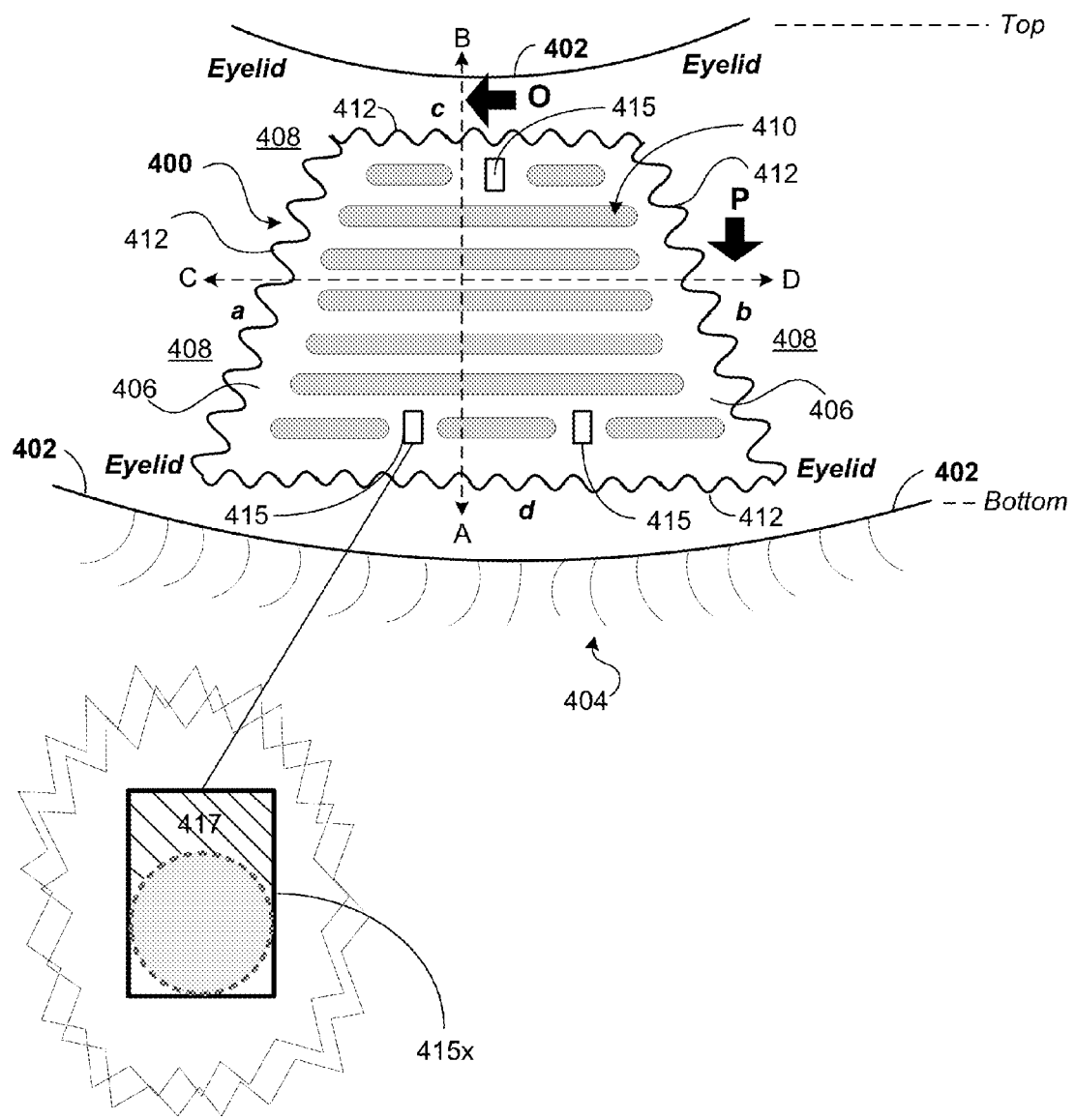
FIG. 4A depicts a front perspective view of an improved exemplary eyelid weight implant device as observed by looking through an eyelid, according to one embodiment.

FIG. 4A depicts a front perspective view of an improved exemplary eyelid weight implant device 400 as observed by looking through an eyelid 402, according to one exemplary embodiment. The improved exemplary eyelid weight implant device 400 include a substantially trapezoidal shape having either three equal sides (a, b, c) or two equal sides (a, b). The base (d) of the trapezoidally shaped implant 400 is locate adjacent to the bottom portion of the eyelid where the lashes 404 are located, whereby the side (c) of the trapezoidally shaped implant 400 that is parallel to the base (d) is located at the top portion of the eyelid. The trapezoidal or triangular shape minimizes the footprint of the implant relative to more symmetrical geometries and also facilitates the movement of the implant in the vertical direction as the eyelid opens and closes.

As further depicted in FIG. 4A, the outer surface 406 of the implant 400 that is in contact with the inner surface 408 of the eyelid includes undulations 410 that enable a stronger bond to occur between the surfaces 406, 408 by creating a means for tissue grabbing based on tissue growth within the undulated structure. It may be appreciated that other non-smooth surfaces having surface irregularities may be used to enable an enhanced contact between the surface 406 of the implant 400 and the eyelid inner surface 408. Also, the sides of the implant 400 are corrugated, as defined by 412, to further contribute to the tissue grabbing and enhancement of the implant's 400 postoperative stability.

The eyelid weight implant device 400 further includes suture holes 415. As illustrated by the expanded view of one of the suture holes 415x, the improved embodiment includes a rectangular shaped suture opening that increases in length to both give more room for the suturing process and provide space for the through-and-through ingrowth of tissue for added stabilization. The width of the rectangle is maintained at approximately the same diameter as conventional suture holes to provide the same lateral stability. However, the extended region 417 allows for more room during suturing and an area for accommodating ingrowth of tissue.

FIG. 4B shows a vertical cross sectional view along axis A-B of the improved exemplary eyelid weight implant device 400 of FIG. 4A. This vertical cross section provides an additional illustration of the undulations 410 on the surface 406 of the implant 400. Specifically, this view of the implant device 400 depicts the ballasting of the implant, which asymmetrically distributes the implant weight between the top half portion of the device L1 and the bottom half portion of the device L2. For example, the top half portion L1 can include 40% of the total weight of the implant device 400, while the bottom half portion L2 can include 60% of the total weight of the implant device 400. The increased weight in the bottom portion contributes to avoiding yaw movement of the implant once inserted in the patient's eyelid. Although, the depicted example illustrates a 40%-60% weight distribution, other weight distributions can be contemplated (e.g., 45%-55%, 65%-35%, 70%-30%, etc.).

The vertical cross sectional view along axis A-B of the improved exemplary eyelid weight implant device of FIG. 4A further shows a tapering of the thickness of the implant 400 towards the horizontal edges of the device, as defined by H1 and H2. Similarly, as depicted in FIG. 4C, a horizontal cross sectional view along axis C-D of the improved exemplary eyelid weight implant device of FIG. 4A also shows a tapering of the thickness of the implant 400 towards the vertical edges of the device, as defined by V1 and V2. The tapered thickness of the implant device 400 enhances the manner in which the device follows the curvature of the eyeball and allows for reduced indentations and favorable cosmetic effects.

As such, based on the above features, the disclosed eyelid weight implant device improves, among other things, eyelid closure and enhance anti-migration (i.e., movement) performance.

What is claimed is:

1. An eyelid implant adapted for placement under an eyelid of a patient's eye, the eyelid implant comprising:
    a trapezoidal shaped body having opposing parallel bases, opposing non-parallel lateral sides, an upper portion, a lower portion, and an eyelid-contacting outer surface;
    a plurality of undulations located on the outer surface of the trapezoidal shaped body adapted to enhance contact between the outer surface of the trapezoidal body and an inner surface of the eyelid, the plurality of undulations extending as parallel rows in a direction between the opposing parallel bases; and
    a corrugated region located along at least a portion of a circumference of the trapezoidal shaped body formed by the opposing parallel bases and opposing non-parallel lateral sides, wherein the eyelid implant is adapted for placement under the eyelid for weighting the eyelid and facilitating eyelid movement, the corrugated region and the plurality of undulations adapted to restrict post-operative movement of the eyelid implant relative to the eyelid by contacting with tissue associated with the eyelid during post-operative healing,
    wherein the upper portion is located above an axis that is both parallel to the opposing parallel bases and equidistant from each of the opposing parallel bases, and the lower portion is located below said axis, wherein the lower portion includes an increased weight distribution relative to the upper portion for facilitating the weighting of the eyelid.

2. The eyelid implant of claim 1, wherein the trapezoidal shaped body comprises a cross-section thickness that tapers in thickness in a direction towards the opposing parallel bases and in a direction towards the opposing non-parallel lateral sides.

3. The eyelid implant of claim 1, wherein the increased weight distribution of the lower portion relative to the upper portion for facilitating the weighting of the eyelid comprises a 60% to 40% weight distribution.

4. The eyelid implant of claim 1, wherein the increased weight distribution of the lower portion relative to the upper portion for facilitating the weighting of the eyelid comprises a 55% to 45% weight distribution.

5. The eyelid implant of claim 1, wherein the increased weight distribution of the lower portion relative to the upper portion for facilitating the weighting of the eyelid comprises a 65% to 35% weight distribution.

6. The eyelid implant of claim 1, wherein the increased weight distribution of the lower portion relative to the upper portion for facilitating the weighting of the eyelid comprises a 70% to 30% weight distribution.

7. The eyelid implant of claim 1, further comprising at least two suture openings comprising rectangular shaped openings, the rectangular shaped openings each having a first and a second region, the first region adapted to receive a suture and the second region adapted to receive a through-and-through ingrowth of tissue during a post-operative healing process, wherein the through-and-through ingrowth of tissue associated with the openings during the post-operative healing process is adapted to provide at least one of a post-operative lateral movement stabilization of the eyelid implant, a post-operative vertical movement stabilization of the eyelid implant, and a post-operative yaw movement stabilization of the eyelid implant.

* * * * *